United States Patent [19]

Sageser

[11] Patent Number: 5,542,943
[45] Date of Patent: * Aug. 6, 1996

[54] ABSORBENT ARTICLE HAVING INFLECTED BARRIER CUFFS AND METHOD FOR MAKING THE SAME

[75] Inventor: David M. Sageser, Cincinnati, Ohio

[73] Assignee: The Procter & Gamble Company, Cincinnati, Ohio

[*] Notice: The term of this patent shall not extend beyond the expiration date of Pat. No. 5,454,803.

[21] Appl. No.: 336,601

[22] Filed: Nov. 9, 1994

Related U.S. Application Data

[63] Continuation-in-part of Ser. No. 299,032, Aug. 31, 1994, Pat. No. 5,454,803, which is a continuation of Ser. No. 178,983, Jan. 7, 1994, abandoned.

[51] Int. Cl.$^6$ .............................. A61F 13/15; A61F 13/20
[52] U.S. Cl. ...................... 604/385.2; 604/386; 604/387
[58] Field of Search ................................ 604/358, 385.1, 604/385.2, 387, 389, 391, 392, 393, 394

[56] References Cited

U.S. PATENT DOCUMENTS

| Re. 26,151 | 1/1967 | Duncan et al. . |
|---|---|---|
| 3,180,335 | 4/1965 | Duncan et al. . |
| 3,658,063 | 4/1972 | Schaar . |
| 3,710,797 | 1/1973 | Marsan . |
| 3,744,494 | 7/1973 | Marsan . |
| 3,776,233 | 12/1973 | Schaar . |
| 3,848,597 | 11/1974 | Endres . |
| 3,860,003 | 1/1975 | Buell . |
| 3,890,973 | 6/1975 | Davis et al. . |
| 3,929,134 | 12/1975 | Karami . |
| 3,938,523 | 2/1976 | Gilliland . |
| 3,939,837 | 2/1976 | Taylor . |
| 3,951,150 | 4/1976 | Schaar . |
| 3,978,860 | 9/1976 | Stima . |
| 3,978,861 | 9/1976 | Schaar . |
| 3,995,638 | 12/1976 | Schaar . |
| 4,040,423 | 8/1977 | Jones, Sr. . |
| 4,085,754 | 4/1978 | Ness et al. . |
| 4,100,922 | 7/1978 | Hernandez . |
| 4,210,143 | 7/1980 | De Jonckheere . |
| 4,246,900 | 1/1981 | Schroder . |
| 4,490,148 | 12/1984 | Beckestrom . |

(List continued on next page.)

FOREIGN PATENT DOCUMENTS

| 2160103 | 12/1985 | United Kingdom . |
|---|---|---|
| 2161059 | 1/1986 | United Kingdom . |
| 2196834 | 5/1988 | United Kingdom . |
| 2197181 | 5/1988 | United Kingdom . |
| WO91/08725 | 6/1991 | WIPO . |
| WO93/14729 | 8/1993 | WIPO . |

*Primary Examiner*—John G. Weiss
*Assistant Examiner*—Mark O. Polutta
*Attorney, Agent, or Firm*—David M. Weirich; Steven W. Miller; Jacobus C. Rasser

[57] ABSTRACT

Absorbent articles having side panels that provide inflected barrier cuffs which promote better containment and fit. The absorbent article has a front waist region, a rear waist region, a crotch region and a pair of longitudinal edges. The absorbent article further comprises a chassis including a pair of longitudinally extending side panels, each of the side panels having a front ear flap section; a barrier cuff section having a first end edge located longitudinally inboard of the front ear flap section; a second end edge located in the rear waist region; a proximal edge and a distal edge; spacing means joined with each barrier cuff section; and closing means for securing at least a portion of the barrier cuff section juxtaposed the first end edge to the absorbent article inboard of the proximal edge. The distal edges are unsecured to any underlying structure of the absorbent article in the front and rear waist regions such that the distal edges form the longitudinal edges in the front and rear waist regions. The distal edge of the barrier cuff section is secured laterally inboard of the proximal edge in the crotch region such that the second end edges of the side panels located in the rear waist region are inverted relative to the first end edges to form an inflected barrier cuff that stands up in the crotch region when the absorbent article is fitted to a wearer.

12 Claims, 10 Drawing Sheets

U.S. PATENT DOCUMENTS

| | | |
|---|---|---|
| 4,505,706 | 3/1985 | Erpicum et al. . |
| 4,596,244 | 6/1986 | Jackson . |
| 4,610,679 | 9/1986 | Matsushita . |
| 4,636,207 | 1/1987 | Buell . |
| 4,681,579 | 7/1987 | Toussant et al. . |
| 4,695,278 | 9/1987 | Lawson . |
| 4,704,115 | 11/1987 | Buell . |
| 4,704,116 | 11/1987 | Enloe . |
| 4,738,677 | 4/1988 | Foreman . |
| 4,743,246 | 5/1988 | Lawson . |
| 4,795,454 | 1/1989 | Dragoo . |
| 4,808,178 | 2/1989 | Aziz et al. . |
| 4,822,435 | 4/1989 | Igaue et al. . |
| 4,834,740 | 5/1989 | Suzuki et al. . |
| 4,846,823 | 7/1989 | Enloe . |
| 4,846,825 | 7/1989 | Enloe et al. . |
| 4,850,987 | 7/1989 | Gilomen . |
| 4,883,482 | 11/1989 | Gandrez et al. . |
| 4,892,528 | 1/1990 | Suzuki et al. . |
| 4,900,317 | 2/1990 | Buell . |
| 4,904,251 | 2/1990 | Igaue et al. . |
| 4,909,803 | 3/1990 | Aziz et al. . |
| 4,964,860 | 10/1990 | Gipson et al. . |
| 5,021,051 | 6/1991 | Hiuke . |
| 5,032,120 | 7/1991 | Freeland et al. . |
| 5,064,489 | 11/1991 | Ujimoto et al. . |
| 5,085,654 | 2/1992 | Buell . |
| 5,087,255 | 2/1992 | Sims . |
| 5,114,420 | 5/1992 | Igaue et al. . |
| 5,167,653 | 12/1992 | Igaue et al. . |
| 5,188,626 | 2/1993 | Toyoda et al. .......... 604/385.1 |
| 5,190,606 | 3/1993 | Merkatoris et al. . |
| 5,445,628 | 8/1995 | Gipson et al. ............ 604/392 |
| 5,454,803 | 10/1995 | Sageser et al. ........... 604/385.2 |

ABSORBENT ARTICLE HAVING INFLECTED BARRIER CUFFS AND METHOD FOR MAKING THE SAME

This application is a continuation-in-part of application Ser. No. 08/299,032 filed on Aug. 31, 1994, which issued as U.S. Pat. No. 5,454,803 on Oct. 3, 1995 to David M. Sageser, et al.; which is a continuation of application Ser. No. 08/178,983 filed on Jan. 7, 1994, which has been abandoned.

FIELD OF THE INVENTION

The present invention relates to absorbent articles such as disposable diapers, incontinence briefs, undergarment absorbent inserts, feminine hygiene garments, and, more particularly, to absorbent articles having side panels that become inflected when the absorbent article is fitted to the wearer to provide barrier cuffs which improve the containment characteristics and fit of the absorbent article.

BACKGROUND OF THE INVENTION

The major function of absorbent articles such as disposable diapers and incontinence briefs or undergarments is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article and the absorbent article is not able to sustain a good fit on the wearer such that gaps are created allowing the exudates to leak out of the absorbent article. For example, urine tends to be deposited onto the topsheet more rapidly than it can be absorbed and, therefore, the urine migrates to the gaps in the absorbent article where it can come in contact with clothing or other articles and can be absorbed by these articles. Additionally, loose fetal material that is not easily absorbed by the absorbent article tends to "float" on the liquid-receiving surface and work its way past the gaps in the article in the legs or waist of the wearer.

Contemporary disposable diapers have a topsheet, a backsheet, an absorbent core, and elasticized leg flaps generally formed from an elastic member being enclosed in the continuous topsheet and backsheet which extend beyond the edges of the absorbent core. These elasticized leg flaps prove effective generally to prevent wicking and overflow from the fluid laden diaper to clothing contacting the edges of the diaper in that the elasticized leg flaps present a fluid impervious barrier between the edge of the diaper and the contacting clothing, and in addition, provide a gasketing action about the legs of the wearer to maintain a seal about the leg and minimize gapping. However, leakage along the perimeter of the diaper may still occur. As the diaper is worn for longer periods of time, forces tend to act on the diaper to degrade the initial fit on the wearer. Large gaps and sagging of the diaper in the legs and waist are formed by the degradation in fit. Thus, as liquids are deposited onto the topsheet, some of the liquid is not immediately absorbed through the topsheet and migrates toward the edges of the diaper where it can leak through or past the gaps in the diaper and come in contact with clothing or undergarments where it can be absorbed by and wicked into such garments.

Disposable diapers may be provided with barrier cuffs which inhibit loose fecal material or gushes of urine or liquids from soiling the wearer's clothing. The barrier cuffs restrain the free flow of this material and provide a structure to hold such material within the diaper so that as such material freely floats or flows on the topsheet of the diaper, it is contained within the diaper. Despite the effectiveness of such structures in containing such material, it has been found that liquids can leak beyond the barrier cuffs and soil the wearer's clothing because the diaper construction does not promote a sustained fit of the diaper on the wearer. Additionally, the barrier cuffs may not be properly applied to the wearer such that good initial fit is not achieved and the sustained fit is often worse.

Examples of some disposable diapers and absorbent articles described in the patent literature are:

U.S. Pat. No. Re 26,151 which reissued Jan. 31, 1967 (originally U.S. Pat. No. 3,180,335, dated Apr. 27, 1965) to Robert C. Duncan discloses a disposable diaper having inwardly folded side flaps and means to fasten the ends of the inwardly folded edges of the side flaps in position over the face of the absorbent pad of the diaper.

U.S. Pat. No. 3,860,003 which issued to Kenneth Barclay Buell on Jan. 24, 1985 discloses contractible side portions for disposable diapers. Such diapers have outwardly extending side flaps and elastic members forming seals about the leg.

U.S. Pat. No. 4,490,148 which issued Dec. 25, 1984 to Bo Beckestrom discloses an incontinence brief or diaper that has inwardly folded side flaps that are fixed at their ends to the backsheet, and which side flaps have elasticized free edges. The Beckestrom patent follows the Duncan teaching that the side flaps are not secured in the crotch area. Beckestrom positions the points of fastening at the ends of the side flaps behind the waistband edges of the absorbent core, and fastens them to underlying portions of the backsheet.

U.S. Pat. No. 4,964,860 issued to Gipson et al. on Oct. 23, 1990 discloses a detachable two piece absorbent article having a disposable element having inflected side panels (FIG. 2). The disposable element is temporarily secured to a refastenable belt which holds the disposable assembly against the waist of the wearer.

U.S. Pat. No. 5,087,255 issued to Bret A. Sims on Feb. 11, 1992 discloses an absorbent article having an inflected barrier leg cuff which provides improved waist containment and fit. While this absorbent article has been effective, it is not economical to manufacture. The barrier leg cuff is manufactured independent of the absorbent core, backsheet and topsheet, and must be positioned and affixed to the topsheet as part of the manufacturing process.

Therefore, it is an object of the present invention to provide an absorbent article which has the improved containment characteristics of the inflected barrier cuff described in the Sims patent and the two piece garment of Gipson et al. but which is more convenient and efficient to manufacture and use.

It is an additional object of the present invention to provide an absorbent article having an inflected barrier cuff which acts as a restraint against the leakage of body exudates.

It is a still further object of the present invention to provide an absorbent article that is easy to apply to the wearer and promotes better containment by being less sensitive to variations in the application of the diaper and providing improved sustained fit.

These and other objects of the invention will be more readily apparent when considered in reference to the following description and when taken in connection with the accompanying drawings.

SUMMARY OF THE INVENTION

The present invention provides absorbent articles such as disposable diapers, incontinence briefs, diaper holders, training pants, feminine hygiene garments, and the like, having inflected barrier cuffs that improve the fit and containment characteristics of the absorbent article which are more convenient and economical to manufacture and use than products currently on the market. The absorbent article of the present invention preferably comprises a chassis having a front waist region; a rear waist region; a crotch region; a liquid pervious topsheet; a liquid impervious backsheet associated with the topsheet; an absorbent core positioned between the topsheet and the backsheet; and a pair of longitudinally extending side panels preferably formed from extensions of the topsheet, the backsheet, or both. The side panels each have a distal edge and a proximal edge, and extend longitudinally from the front waist region through the crotch region to the rear waist region. The side panels further comprise a spacing means disposed adjacent the distal edge of each side panel in the crotch region.

In one preferred embodiment, the side panels are folded inwardly and bonded to the topsheet in the crotch region, while the side panels are outwardly folded in at least the rear waist region. Thus, when fitted to the wearer, the side panels become inflected along their length. This transitions the side panels from their snug, gasketing fit about the buttocks of the wearer to their stand-up configuration in the "no motion zones" of the crotch region. The resulting "inflected barrier cuff" positioned in the no motion zones of the crotch region of the wearer provides improved fit and containment characteristics throughout the time of use. The side panels can also be extended laterally outwardly in the front waist region to form front ear flaps that provide for better containment and a wider range of wearer sizes.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
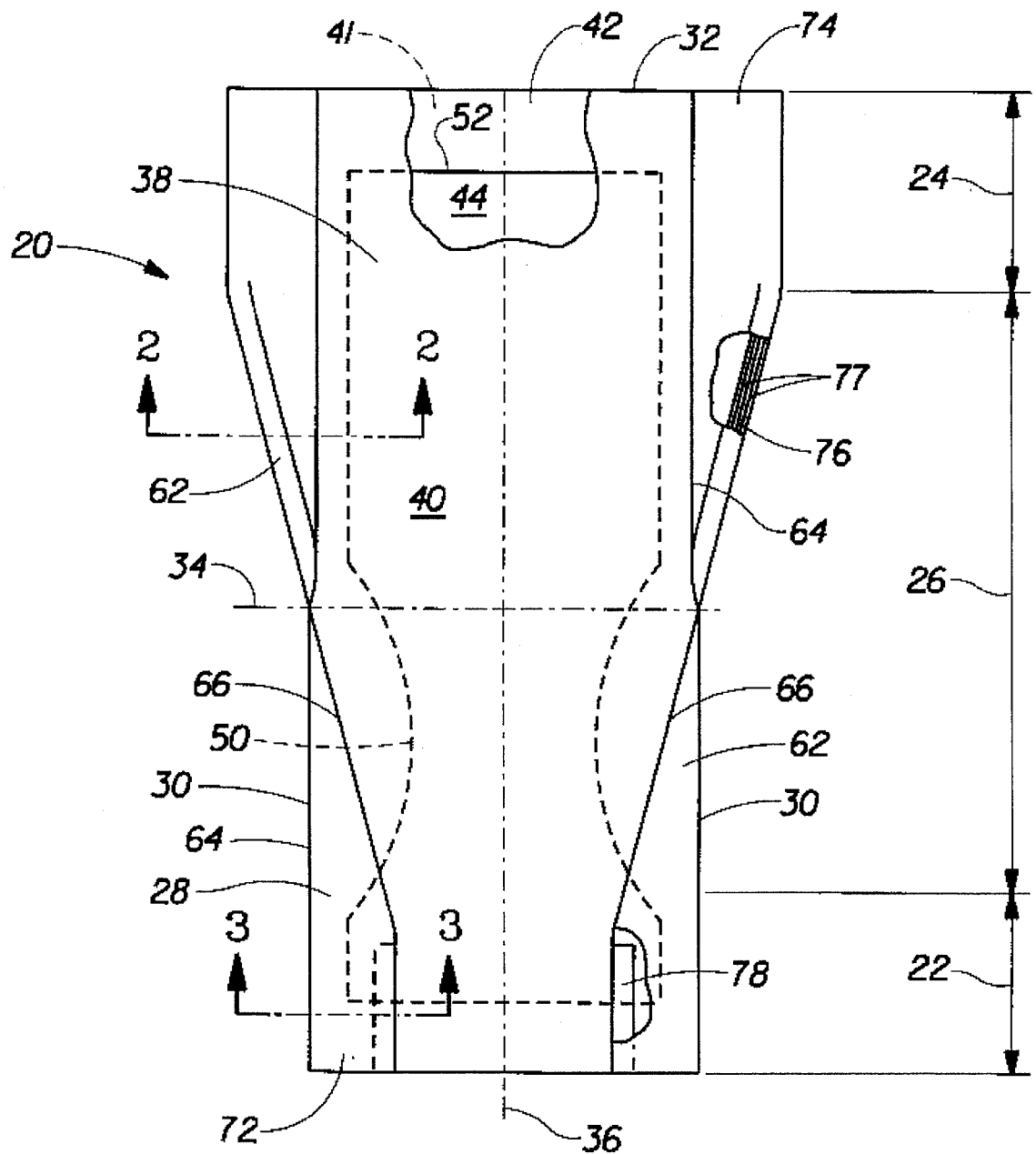
FIG. 1 is a perspective view of a disposable diaper embodiment of the present invention having portions cut away to reveal underlying structure, the body-facing surface of the diaper facing the viewer.

As used herein, the term "absorbent article" refers to articles which absorb and contain body exudates and more specifically refers to articles which are placed against or in proximity to the body of the wearer to absorb and contain the various exudates discharged from the body. Absorbent articles are typically differentiated by whether they are reusable or disposable. "Disposable" refers to articles which are intended to be discarded after a single use (i.e., they are not intended to be laundered or otherwise restored or reused). The absorbent articles of the present invention are preferably disposable absorbent articles. The absorbent articles may be further defined by whether they are "unitary" such that they do not require separate manipulative parts or whether they comprise an element of a diaper system such as a separate holder and liner. The absorbent articles of the present invention are preferably unitary. A preferred embodiment of a unitary disposable absorbent article of the present invention, diaper 20, is shown in FIG. 1. As used herein, the term "diaper" refers to a garment generally worn by infants and incontinent persons about the lower torso of the wearer. It should be understood, however, that the present invention is also applicable to other disposable absorbent articles such as incontinence briefs, undergarment absorbent inserts, disposable training pants, belted diapers, diaper holders, sanitary napkins, and the like.

FIG. 1 is a plan view of one preferred embodiment of diaper 20 of the present invention in its flat-out, uncontracted state (i.e., with all elastic induced contraction pulled out) with portions of the structure being cut-away to more clearly show the construction of the diaper 20 and with the portion of the diaper 20 which contacts the wearer facing the viewer. The diaper 20 is shown in FIG. 1 to have a body-facing surface 40 (facing the viewer in FIG. 1), a garment-facing surface 41 opposed to the body-facing surface 40, a front waist region 22, a rear waist region 24, a crotch region 26, and a periphery which is defined by the outer edges of the diaper 20 in which the longitudinal edges are designated 30 and the end edges are designated 32. The waist regions generally comprise those portions of the diaper 20 which, when worn, encircle the waist of the wearer. The waist regions may include an elastic element such that they gather about the waist of the wearer. The crotch region 26 is that portion of the diaper 20 positioned between the front waist region 22 and the rear waist region 24, and comprises that portion which, when worn, is positioned between the legs of the wearer and covers the lower torso of the wearer. The diaper 20 also has a lateral centerline which is designated 34 and a longitudinal centerline which is designated 36.

The diaper 20 comprises a liquid pervious topsheet 38; a liquid impervious backsheet 42 having an inner surface 23 (shown in FIGS. 2–4) and an outer surface 28 opposed to the inner surface 23; an absorbent core 44 having side edges that are designated side edges 50 and waist edges 52; side panels 62 each having a proximal edge 64, a distal edge 66, a first end 72, and a second end 74; spacing means 76 such as elastic members 77 for spacing the distal edge 66 away from the body-facing surface 40; and closing means 78 for securing at least a portion of the side panel 62 inboard of the proximal edge 64 in the front waist region 22.

Figure 2:
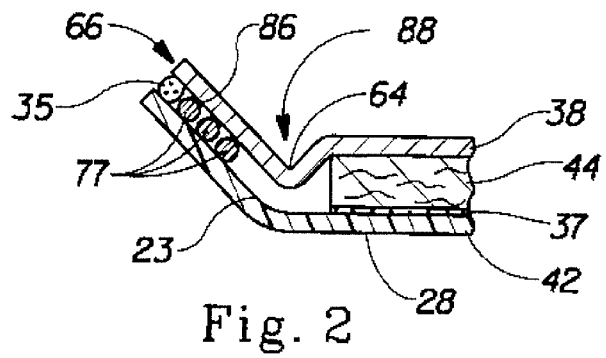
FIG. 2 is a fragmentary sectional view taken along section line 2—2 of FIG. 1.

In a preferred embodiment of the diaper 20 in which the backsheet 42 has length and width dimensions generally larger than those of the absorbent core 44, the backsheet 42 extends beyond the edges of the absorbent core 44 to thereby form the periphery of the diaper 20 and the side panels 62. The periphery defines the outer perimeter or, in other words, the edges of the diaper 20. The periphery comprises the longitudinal edges 30 and the end edges 32. As shown in FIGS. 1 and 2, the topsheet 38 may be coterminous with the backsheet 42 along the end edges 32 as well as the longitudinal edges 30 of the diaper 20.

Preferably, the proximal edge 64 of the side panel 62 defines the longitudinal edge 30 of the diaper 20 in the front waist region 22, and preferably comprises an extension of the topsheet 38 or the backsheet 42, or both. The distal edge 66 of each side panel 62 defines the longitudinal edge 30 of the diaper 20 in the rear waist region 24. The distal edge 66 is preferably not secured to any underlying elements of the diaper 20 in the crotch region 26 or the rear waist region 24. However, the distal edge 66 is preferably secured to the underlying structure (topsheet 38) of the diaper 20 laterally inboard of the proximal edge 64 in the front waist region 22 by the closing means 78, which preferably comprises an adhesive. (As used herein, the term "laterally inboard" is defined as the direction toward the longitudinal centerline 36 of the diaper 20.) Therefore, the distal edge 66 is closed in the front waist region 22 (i.e., it is not open nor capable of being spaced away from the body-facing surface 40).

FIG. 2 is a fragmentary sectional view taken along line 2—2 of FIG. 1 and depicts one preferred construction of the side panel 62 showing the topsheet 38, the backsheet 42, the absorbent core 44, and the elastic members 77. The absorbent core 44 is disposed between the topsheet 38 and the backsheet 42; the topsheet 38 and the backsheet 42 extending beyond the side edge 50 of the absorbent core 44 to form the side panel 62. In the embodiment shown, the topsheet 38 is secured to the backsheet 42 along the distal edge 66 by a bead of adhesive 35. Preferably, a layer of adhesive 37 is used to secure the absorbent core 44 to the backsheet as described later. The spacing means 76, such as a plurality of elastic members 77, is joined adjacent the distal edge 66 of each side panel 62. Preferably, an elastic attachment means 86 joins the elastic members 77 to the diaper 20. The distal edge 66 is thus spaced away from the body-facing surface 40 of the topsheet 38 by the elastic gathering action of the elastic members 77; a channel 88 being thereby formed between the proximal edge 64 and the distal edge 66.

Figure 3:
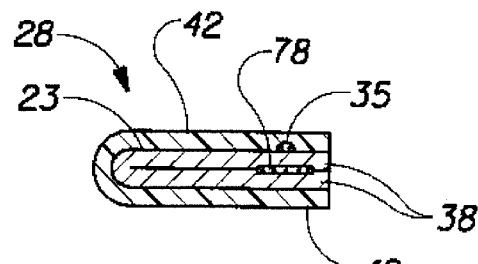
FIG. 3 is a fragmentary sectional view taken along section line 3—3 of FIG. 1.

FIG. 3 is a fragmentary sectional view taken along line 3—3 of FIG. 1 and depicts one preferred construction of the side panels 62 in the front waist region 22. The topsheet 38 and the backsheet 42 extend beyond the side edge 50 of the absorbent core 44 to form the side panels 62. As shown in FIG. 3, the topsheet 38 is folded upon itself and secured by the first closing means 78. In the embodiment shown, the outer surface 28 of the backsheet 42 is adjacent the skin of the wearer when the garment is donned. Therefore, it is desirable to adopt designs in which the outer surface 28 is formed from or is covered with cloth or a cloth-like substitute such that a skin-friendly surface is provided against the wearer's skin.

The absorbent core 44 may be any absorbent material which is generally compressible, conformable, non-irritating to the wearer's skin, and capable of absorbing and retaining liquids and certain body exudates. The absorbent core 44 may be manufactured in a wide variety of sizes and shapes (e.g., rectangular, hourglass, asymmetric, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent core 44 should, however, be compatible with the design exudate loading and the intended use of the diaper 20. Further, the absorbent capacity and configuration of the absorbent core 44 may be varied to accommodate wearers ranging from infants through adults (e.g., the absorbent core may have a varying caliper, or a hydrophilic gradient, a capillary differential, low density zones, or may or may not contain absorbent gelling materials).

The absorbent core 44 may comprise a layer of absorbent material comprising hydrophilic fibers and particles of absorbent gelling material (hydrogel) such as the absorbent structure described in U.S. Pat. No. 4,610,678 entitled "High-Density Absorbent Structure" which issued to Paul T. Wiseman and Steven A. Goldman on Sep. 9, 1986 and which patent is incorporated herein by reference. Preferred embodiments of the absorbent core 44 are generally described in U.S. Pat. No. 5,234,423 entitled "Absorbent Article With Elastic Waist Feature and Enhanced Absorbency", issued to Alemany et al. on Aug. 10, 1993; and U.S. Pat. No. 5,217,445 entitled "Absorbent Structures Containing Superabsorbent Material and Web of Wetlaid Stiffened Fibers" issued to Young et al. on Jun. 8, 1993, which are incorporated herein by reference. Other exemplary absorbent cores useful in the present invention are described in U.S. Pat. No. 5,124,188 entitled "Porous, Absorbent, Polymeric Macrostructures and Methods of Making the Same", issued to Roe et al., on Jun. 23, 1992; U.S. Pat. No.

5,137,537 entitled "Absorbent Structure Containing Individualized, Polycarboxylic Acid Crosslinked Wood Pulp Cellulose Fibers", issued to Herron et al., on Aug. 11, 1992; U.S. Pat. No. 5,180,622 entitled "Absorbent Members Containing Interparticle Crosslinked Aggregates", issued to Berg, et al., on Jan. 19, 1993; U.S. Pat. No. 5,260,345 entitled "Absorbent Foam Materials for Aqueous Body Fluids and Absorbent Articles Containing Such Materials" issued to DesMarais et al., on Nov. 9, 1993; U.S. Pat. 4,673,402 entitled "Absorbent Article With Dual-Layered Cores" which issued to Paul T. Weisman, Dawn I. Houghton and Dale A. Gellert on June 16; and PCT Publication No. WO 92/11830, published on Jul. 23, 1992, entitled "Absorbent Article Having Rapid Acquiring, Multiple Layer Absorbent Core". All of these patents and patent applications are incorporated herein by reference.

The backsheet 42 is positioned adjacent the absorbent core 44 adjacent the surface that faces away from the wearer and is preferably secured thereto by core attachment means 37 such as those well known in the art. For example, the backsheet 42 may be secured to the absorbent core 44 by a uniform continuous layer of adhesive, a patterned layer of adhesive, or an array of separate lines or spots of adhesive. A adhesives which has been found to be satisfactory is manufactured by H. B. Fuller Company of St. Paul Minn. and marketed as HL-1258. The core attachment means preferably comprise an open pattern network of filaments of adhesive as is shown in U.S. Pat. No. 4,573,986 entitled "Disposable Waste-Containment Garment" which issued to J. A. Minetola and David R. Tucker on Mar. 4, 1986, and which is incorporated herein by reference. An exemplary attachment means of an open pattern network of filaments comprises several lines of adhesive filaments swirled into a pattern such as is illustrated by the apparatus and methods shown in U.S. Pat. No. 3,911,173 issued to Sprague, Jr. on Oct. 7, 1975; U.S. Pat. No. 4,785,996 issued to Zieckler, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 42 is impervious to liquids and is preferably manufactured from a thin plastic film, although other flexible liquid impervious materials may also be used. The backsheet 42 prevents the exudates absorbed and contained in the absorbent core 44 from wetting articles which contact the diaper 20 such as bedsheets and undergarments. Further, the backsheet 42 may permit vapors to escape from the absorbent core 44 while still preventing exudates from passing through the backsheet 42. The backsheet 42 may thus comprise a woven or nonwoven material, polymeric films such as thermoplastic films of, for example, polyethylene or polypropylene, or composite materials such as film-coated nonwoven materials. Alternatively, the backsheet 42 may comprise a laminate of a nonwoven layer and a polymeric film, including embodiments wherein the nonwoven layer extends beyond the dimensions of the polymeric film. An exemplary backsheet 42 is a polyethylene film having a thickness of from about 0.012 mm (0.5 mil) to about 0.051 cm (2.0 mils). As used herein, the term "flexible" refers to materials which are compliant and which will readily conform to the general shape and contours of the human body. A suitable polyethylene film is manufactured by Tredegar Film Products, Inc. of Terre Haute, Ind., and is marketed in the trade as Tredegar X8526. The backsheet 42 is preferably embossed and/or matte finished to provide a more cloth like appearance.

The topsheet 38 is compliant, soft feeling, and non-irritating to the wearer's skin. Further, the topsheet 38 is liquid pervious permitting liquids to readily penetrate through its thickness. A suitable topsheet may be manufactured from a wide range of materials, such as porous foams, reticulated foams, formed films, apertured plastic films, natural fibers (e.g., wood or cotton fibers), synthetic fibers (e.g., polyester or polypropylene fibers) or from a combination of natural and synthetic fibers. There are a number of manufacturing techniques which may be used to manufacture the topsheet 38. For example, the topsheet 38 may be woven, non-woven, spunbonded, carded, or the like. One preferred topsheet 38 comprises staple length polypropylene fibers having a denier of about 2.2, such as P-8, manufactured by Veratec, Inc., a Division of the International Paper Company, of Walpole, Mass. As used herein, the term "staple length fibers" refers to those fibers having a length of at least about 15.9 mm (0.625 inches). A preferred topsheet 38 is carded, and thermally bonded by means well known to those skilled in the fabrics art.

In a preferred embodiment, the topsheet 38 is made of a hydrophobic material to isolate the wearer's skin from liquids in the absorbent core 44. If the topsheet 38 is made of a hydrophobic material, at least the upper surface of the topsheet 38 is treated to be hydrophilic so that liquids will transfer through the topsheet 38 more rapidly. This diminishes the likelihood that body exudates will flow off the topsheet 38 rather than being drawn through the topsheet 38 and being absorbed by the absorbent core 44. The topsheet 38 can be rendered hydrophilic by treating it with a surfactant including spraying the topsheet 38 material with a surfactant or immersing the material into the surfactant. A more detailed discussion of such a treatment is contained in U.S. Pat. No. 4,988,344 entitled "Absorbent Articles with Multiple Layer Absorbent Layers" issued to Reising et at., on Jan. 29, 1991, and U.S. Pat. No. 4,988,345 entitled "Absorbent Articles with Rapid Acquiring Absorbent Cores" issued to Reising on Jan. 29, 1991, each of which is incorporated herein by reference.

The topsheet 38 and the backsheet 42 may be joined together in any suitable manner as is well known in the diaper manufacturing art. As used herein, the term "joined" encompasses configurations whereby the topsheet 38 is directly joined to the backsheet 42 by affixing the topsheet 38 directly to the backsheet 42, and configurations whereby the topsheet 38 is indirectly joined to the backsheet 42 by affixing the topsheet 38 to intermediate members which in turn are affixed to the backsheet 42. In a preferred embodiment, the topsheet 38 and the backsheet 42 are joined directly to each other in the diaper periphery by attachment means 35 such as an adhesive or any other attachment means as is known in the art. Suitable attachment means are discussed previously with regard to the backsheet 42.

The diaper 20 further comprises a pair of side panels 62 that provide a structure to restrain the free flow of body exudates along the body-facing surface 40 of the diaper 20, and to hold and contain such exudates within the diaper 20. In a preferred embodiment, the side panels 62 are liquid impermeable. Thus, in the front waist region 22, where the side panels 62 are folded over the body-facing surface 48 of the absorbent core 44, the side panels 62 prevent liquid deposited on the topsheet 38 from migrating beyond the absorbent core 44. This helps ensure that any liquids not immediately absorbed by the absorbent core 44 will be absorbed before they migrate to areas from which the liquids can leak out of the diaper 20. In the crotch region 26, the side panels 62 stand-up in the "no motion" zones of the wearer and provide a liquid impermeable barrier cuff that conforms to the wearer's body providing containment of body exudates well beyond when the diaper 20 has been loaded. In the rear waist region 24, the side panels 62 provide a gasketing action about the buttocks of the wearer that helps prevent gapping that can lead to leaks.

Each side panel 62 is a flexible member having a proximal edge 64 and a distal edge 66. The distal edge 66 of the side panel 62 is that part of the side panel 62 that is spaced laterally outwardly from the absorbent core 44 when the side panel 62 is in a flat-out state (before the side panel 62 is folded and joined to the topsheet 38 in the front waist region 22). The distal edge 66 of each side panel 62 is preferably not secured to any underlying elements of the diaper 20 in at least the rear waist region 24, preferably in both the rear waist region 24 and the crotch region 26. The distal edge 66 is preferably spaced away from the body-facing surface 40 in the crotch region 26 so that the side panel 62 may form a channel 88 (as shown in FIG. 2) to enhance the containment of the diaper 20. As used herein, "spaced" includes embodiments wherein the distal edges 66 may assume one or more positions relative to the body-facing surface 40 including at some times assuming a position adjacent the body-facing surface 40. In a preferred embodiment, as shown in FIG. 1, the distal edge 66 of each side panel 62 is disposed laterally inboard of the proximal edge 64 in the front waist region 22 so as to present a more effective barrier against the flow of exudates. The distal edges 66 are maintained inboard of the proximal edges 64 in the front waist region 22 by the first closing means 78 so as to obviate their inversion.

The proximal edge 64 is that portion of the side panel 62 that is disposed adjacent the side edges 50 of the absorbent core 44. (When the side panels 62 are in a flat-out configuration, the proximal edge 64 is spaced laterally inboard from the distal edge 66.) The distal edge 66 is spaced apart from the proximal edge 64 and their spatial relationship to each other defines the effective width of each of the side panels 62. The proximal edges 64 and the distal edges 66 may be in a parallel, nonparallel, rectilinear or curvilinear relationship. In addition, each of the side panels 62 may have a variety of different cross-sectional areas including circular, square, rectangular or any other shape. Preferably, the proximal edge 64 is spaced from the distal edge 66 in a parallel and rectilinear relationship. The effective width of the side panel 62 is an important parameter in reducing leakage of body exudates out of the diaper 20. If the effective width of the side panel is too small, then gaps will be formed between the leg of the wearer and the distal edge 66 such that liquids may flow over the distal edge 66 to the periphery of the diaper 20.

As shown in FIG. 1, the distal edges 66 are preferably laterally spaced apart from each other in the front waist region 22. However, the lateral spacing between the distal edges 66 can range from being crossed over each other to abutting each other to being laterally spaced apart up to the width of the proximal edges in the front waist region 22. Thus, in a preferred embodiment as shown in FIG. 1, the distal edges 66 may be laterally spaced apart from about −25 mm (−1 inch) (overlapping edges) up to about 150 mm (6 inches). Preferably, the distal edges 66 are spaced apart so that the side panel will fit in the innermost leg crease of the wearer rather than ride along the wearer's outer thigh.

The distal edges 66 are also shown in FIG. 1 to be disposed parallel to each other and perpendicular to the end edge 32 of the diaper 20 in the front waist region 22. While this is a preferred embodiment, the distal edges 66 may alternatively be angled toward or away from each other, preferably toward each other, such that the distal edges 66 are disposed non-perpendicular to the end edges 32. Angling the side panels 62 relative to the end edge 32 may assist in allowing the side panel 62 to remain spaced from the body-facing surface 40 in the crotch region 26 during use.

The distal edges 66 are preferably laterally spaced apart from each other in the crotch region 26. The lateral spacing of the distal edges 66 is especially important in the crotch region 26 to prevent body exudates, especially urine, from leaking out of the diaper 20 in the leg regions of the wearer. If the distal edges 66 are laterally spaced too far from each other, then the side panels 62 have an increased tendency to "flip out" in the crotch region 26 such that urine can flow over the side panels 62. If the distal edges 66 are spaced too close to each other, then the side panels 62 provide a reduced area for deposition of exudates such that exudates could be deposited directly onto the side panels 62 and flow to the edges of the diaper 20.

The distal edge 66 of each side panel 62 is preferably disposed laterally outboard of each proximal edge 64 in the rear waist region 24 of the diaper 20 when the diaper 20 is in a flat-out uncontracted condition. The term "outboard" is defined as the direction away from the longitudinal centerline 36 of the diaper 20. (i.e., the direction opposite from the direction defined by the term "inboard.") Thus, the side panel 62 extends laterally outwardly in the rear waist region 24 when the diaper 20 is in a flat-out uncontracted condition. The laterally extending portion of the side panel 62 promotes better containment that is less sensitive to application variations and provides a sustained contoured fit about the buttocks of the wearer.

Because the distal edge 66 is disposed inboard of the proximal edge 64 in the front waist region 22 and outboard of the proximal edge 64 in the rear waist region 24, the distal edge 66 becomes "inflected" along its length when the diaper 20 is fitted to a wearer. This inflection transitions the side panels 62 from snugly fitting about the buttocks (the laterally outwardly extending portion) to standing up in the "no motion" zone of the crotch region 26 for better containment. The resultant "inflected barrier cuff" is easier to apply to the wearer and ensures that the fit of the side panel 62 is in the "no motion" zone in the crotch region 26 with a snug fit about the wearer's buttocks in at least the rear waist region 24.

It has been found that the inflected barrier cuff thus provides both a gasketing action about the buttocks of the wearer to provide a sustained snug fit which reduces leakage of body exudates, especially runny BM, and a stand-up barrier cuff in the crotch region 26 and the front waist region 22 to constrain, contain and hold body exudates within the diaper along the channel 88. However, it has been found that if the side panel 62 is "flipped out" too far toward the front waist region 22 along the length of the side panel 62, then body exudates will tend to flow over the side panels 62. Thus, it is preferred that the inflected barrier cuffs, in use, provide a gasketing action about the buttocks of the wearer to provide a snug fit (i.e., the flipped out portion of the barrier cuffs is positioned) in less than about 50% of the length of the diaper, more preferably less than about 40% of the length of the diaper 20, and most preferably only in the rear waist region 24. (The percent length of the flipped out portion is defined as that length of the diaper in which the side panel is flipped out divided by the total length of the diaper times 100%.) Thus, the stand-up portion of the side panel (distal edge 66 disposed inboard of the proximal edge 64) is provided, in use, in at least about 50% of the length of the diaper, preferably at least about 60% of the length of the diaper, and most preferably from the front waist region 22 to and throughout the crotch region 26.

Figure 7:
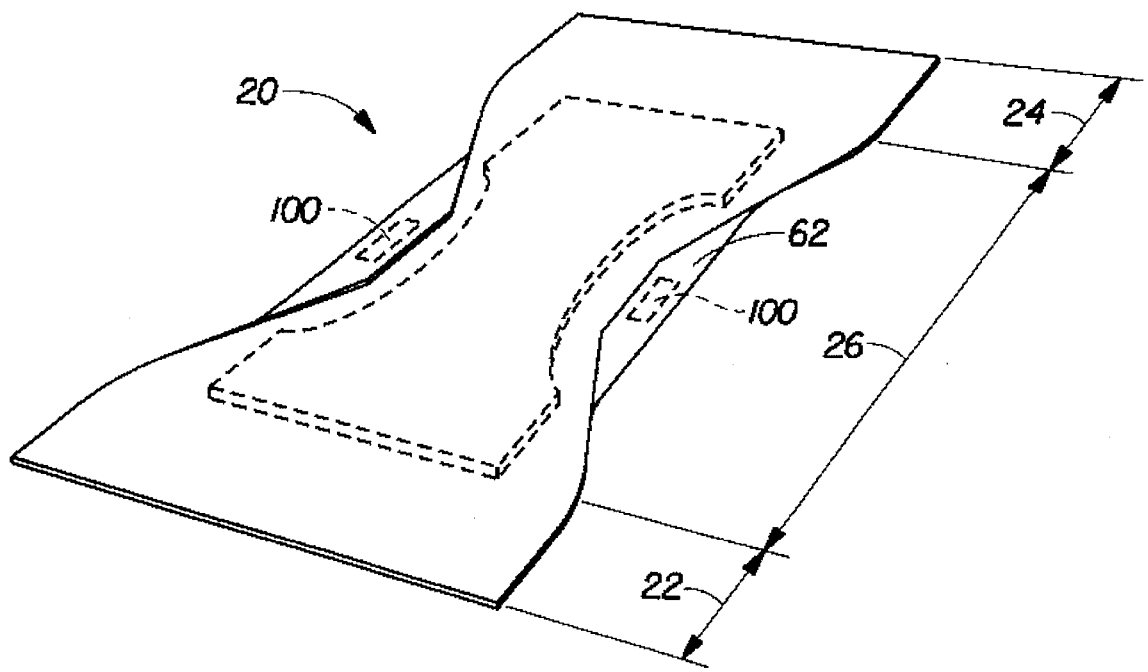
FIG. 7 is a perspective view illustrating another absorbent article in accordance with the present invention in which the side panels are inflected in the crotch region of the garment, the body-facing surface of the diaper facing the viewer.

The flipped out portion of the side panel 62 can be maintained in less than about 50% of the length of the diaper 20 in a number of different ways. For example, the closure means 78 can extended in the longitudinal direction, thus ensuring that the flipped out portion is maintained in less than about 50% of the length of the diaper 20. Alternatively, as shown in FIG. 7, a crotch attachment means 100 may be disposed in the crotch region 26 of the diaper 20 for securing the distal edge 66 inboard of the proximal edge 64.

The crotch attachment means 100 can comprise any attachment means as is known in the art, including those described below with respect to the closure means 78 that maintains the distal edges 66 inboard of the longitudinal edges 30 in the front waist region 22. Further, the bond provided by crotch attachment means 100 may be breakable such that the user may release all or a portion of the distal edge 66 in the crotch region 26 to obtain the desired fit.

The closing means 78 for securing the first end 72 of the side panels 62 closed is shown in FIG. 1. The closing means 78 provides a more comfortable fit for the wearer and secure the distal edges 66 of the side panels 62 in the proper position to form an inflected barrier cuff. In a preferred embodiment as shown in FIG. 1, the closing means 78 is disposed in the front waist region 22. The remaining portions of the distal edges 66 are preferably not secured to any underlying structure of the diaper 20 so that the distal edges 66 are left freely openable. In a preferred embodiment, the length of the closure means 78 is from about 25 mm (about 1 inch) to about 100 mm (about 4 inches), more preferably between about 35 mm (about 1.5 inches) and about 75 mm (about 3 inches). This construction is preferred so as to create a snug fit about the buttocks of the wearer to especially prevent leakage of loose fecal material.

While each of the closing means 78 may comprise any of several securement means as are known in the an such as ultrasonic bonds or heat/pressure bonds or seals using a variety of bonding patterns, or adhesives and/or glues, the closing means are preferably adhesive beads consisting of adhesive such as manufactured by H. B. Fuller Company of St. Paul Minn. and marketed as HL-1258.

As shown in FIG. 1, the spacing means 76 preferably comprise elastic members 77 that are operatively associated with each of the side panels 62 adjacent the distal edge 66. The elastic members 77 are preferably secured to the side panels 62 in an elastically contractible condition so that in a normally unrestrained configuration, the elastic members 77 effectively contract or gather the distal edge 66 of the side panels 62. The elastic members 77 can be secured to the side panels 62 in an elastically contractible condition in at least two ways as is discussed in U.S. Pat. No. 3,860,003 entitled "Contractible Side Portion For Disposable Diaper", which issued to Kenneth B. Buell on Jan. 26, 1974, which is incorporated by reference herein. In addition, the length of the elastic member 77 in general is dictated by the diaper design. In the embodiment illustrated in FIG. 1, the elastic member 77 extends along essentially the entire length of the side panels 62 in the crotch region 26, although other lengths are cognizable. The elastic members 77 are preferably not disposed in the front waist region 22. The lack of gathering of the distal edge 66 adjacent the end edge 32 helps reduce the forces which tend to pull the diaper 20 downward, resulting in sagging and gapping of the diaper 20 in the waist regions.

Figure 8:
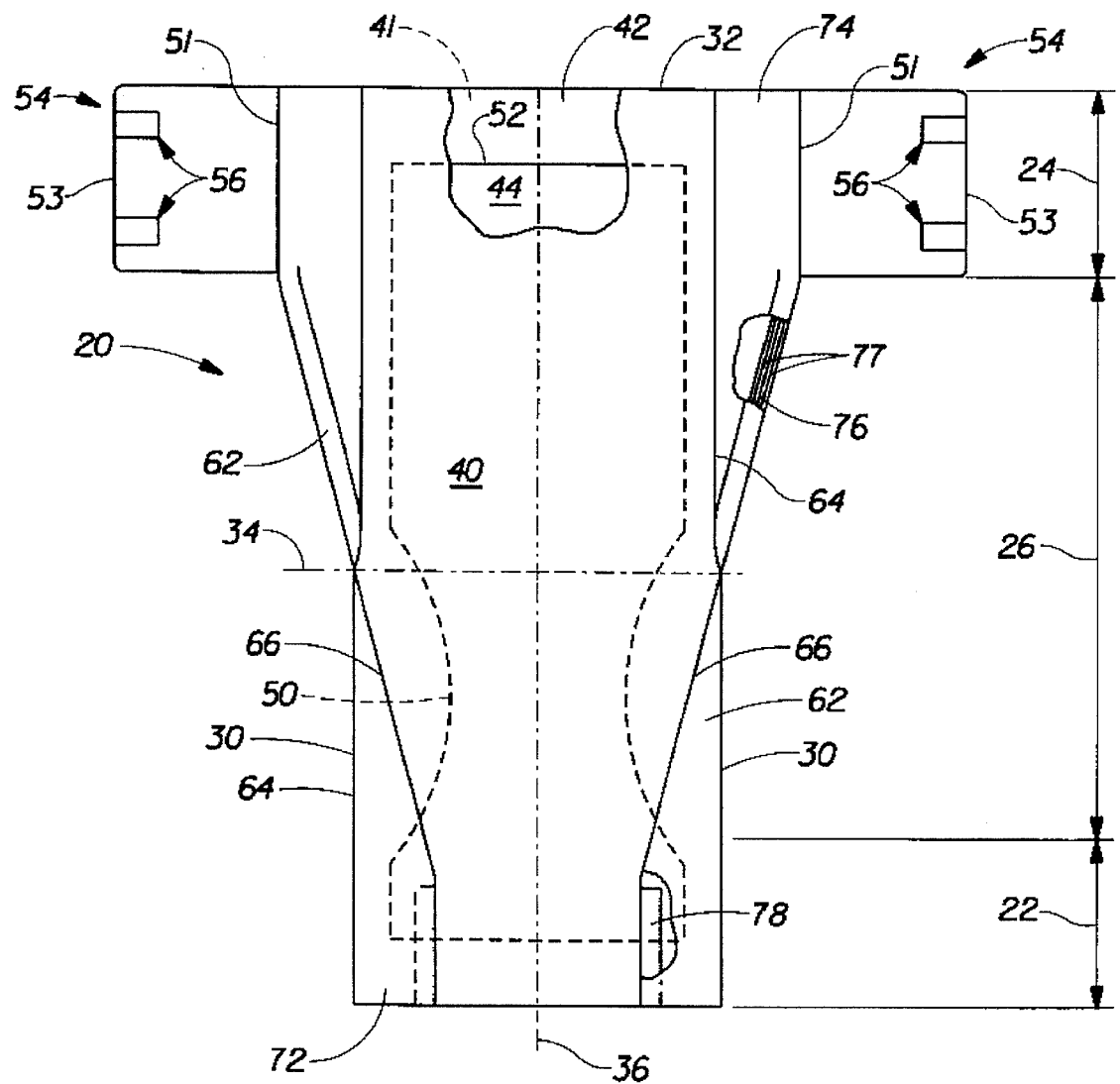
FIG. 8 is a perspective view of another disposable diaper embodiment of the present invention having ear flaps in the rear waist region, the body-facing surface of the diaper facing the viewer.

As shown in FIG. 2, the elastic member 77 is operatively associated with the side panels 62 by securing it to or within the side panels 62 with an elastic attachment means 86. The elastic attachment means 86 should be flexible and of sufficient adhesiveness to hold the elastic member 77 in its stretched condition. While the elastic members 77 may be secured to the side panels 62 adjacent only the ends of the elastic member 77, it is preferable to secure the entire length of the elastic member 77 to the side panels 62. (In one preferred embodiment of the present invention, wherein the absorbent article comprises ear flaps 54 (as shown in FIG. 8), the elastic members 77 may be joined to the ear flaps 54 in the rear waist region 24.) The elastic attachment means 86 herein are preferably glue beads made of hot melt adhesive such as marketed by Findley Adhesives Incorporated, Elmgrove, Wis., as Findley Adhesives 581, although the elastic members 77 may be affixed to the side panels 62 in any of several other ways which are well known in the art. For example, the elastic members 77 may be ultrasonically bonded or heat/pressure sealed into the side panels 62 using a variety of bonding patterns, or the elastic members 77 may simply be glued to the side panels 62. A more detailed description of the manner in which the elastic members 77 may be positioned and secured to the side panels 62 can be found in U.S. Pat. No. 4,081,301, entitled "Method and Apparatus for Continuously Attaching Discrete, Stretched Elastic Strands to Predetermined Isolated Portions of Disposable Absorbent Products" which issued to Kenneth B. Buell on Mar. 28, 1978, and in U.S. Pat. No. 4,253,461, entitled "Absorbent Brief" issued to Danny L. Strickland and Ronald B. Visscher on Mar. 3, 1981, both of which are incorporated herein by reference. It should be noted that one or more (a plurality of) elastic members 77 can be used to elasticize each side panel 62. Preferably, three elastic members 77 are used to elasticize each side panel 62.

An elastic member 77 which has been found suitable is an elastic strand having a cross section of 0.18 mm by 1.5 mm and made from natural rubber as available from Easthampton Rubber Company of Stewart, Va., under the trademark L-1900 Rubber Compound. Other suitable elastic members 77 can be made from natural rubber, such as elastic tape sold under the trademark Fulflex 9411 by Fulflex Company of Middletown, R.I. The elastic member 77 may also comprise any heat shrinkable material as is well known in the art. Other suitable elastic materials may comprise a wide variety of materials as are well known in the art include elastomeric films, polyurethane films, Lycra, elastomeric adhesives, elastomeric foams and formed elastic scrim. In addition, the elastic members 77 may take a multitude of configurations. For example, the width of the elastic members 77 may be varied; the elastic members may comprise a single strand or several parallel or non-parallel strands of elastic material; or the elastic members 77 may be rectilinear or curvilinear.

The spacing means 76 may alternatively comprise several other elements. For example, the side panels 62 may have stiffening means disposed in or on each side panel 62. The stiffening means must be sufficiently stiff so that the distal edge 66 is spaced away from the body-facing surface 40. Suitable materials for the stiffening means include foams, nonwoven fabrics, batting, polyethylene film, formed films, spray glues, foamed elastomerics, polyester, polyurethane, or high loft material.

The spacing means 76 may also comprise means for shortening the length of the distal edge 66 in comparison to the length of the edge of the diaper 20. The distal edge 66 can be shortened by making a fold or pleat in the distal edge 66. This fold or pleat is secured by any of the holding means well known to those of ordinary skill in the art, such as adhesives, or heat sealing. Alternatively, a section may be cut out of the distal edge 66 and the resultant edges brought together to form a butt or lap joint. The distal edge 66 may also be shortened by attaching a length of the distal edge 66 to the topsheet 38 at a position different from where the distal edge 66 would lie when the diaper 20 is in a flattened out condition. Other shortening means as are known in the art can also be used.

The manner in which the diaper 20 is applied to a wearer will vary depending on the embodiment that is being used. Thus, the preferred methods for using the different embodiments are described in more detail below. In each case, however, the distal edges 66 of the side panels 62 are pulled laterally outwardly such that the distal edges 66 are disposed outboard of the proximal edges 64 in the rear waist region 26. This provides a gasketing configuration about the buttocks of the wearer. The distal edges 66 of the side panels 62 remain inboard of the longitudinal edges 30 in the front waist region 22. Thus, the side panels 62 become inflected, forming barrier cuffs that stand-up in the wearer's "no motion" zone in the crotch region 26.

Figure 4:
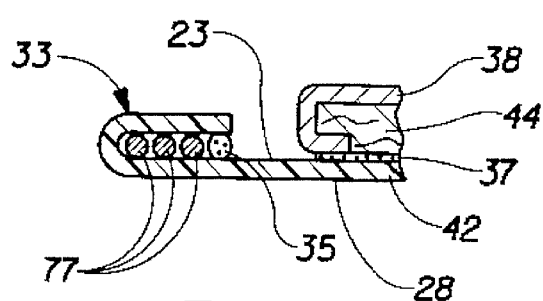
FIG. 4 is a fragmentary sectional view of an absorbent article in accordance with an alternative embodiment of the invention.

FIG. 4 is a fragmentary sectional view of an alternative embodiment of the present invention taken in the front waist region 22. In this embodiment, the topsheet 38 folds around the side edges 50 of the absorbent core 44. Preferably, at least a portion of the topsheet 38 extends between the backsheet 42 and the garment-facing side 46 of the absorbent core 44. The topsheet 38 and the absorbent core 44 are preferably joined to the backsheet 42 using a layer of adhesive 37 or any other means as are known in the art. Further, as shown in FIG. 4, the backsheet 42 includes a longitudinal hem 33 enclosing the elastic members 77. The hem 33 is preferably formed by wrapping a portion of the backsheet 42 around the elastic members 77 and securing the backsheet 42 to itself, inboard of the elastic members 77, with a bead of adhesive 35. Preferably, the backsheet 42 is wrapped around the elastic members 77 such that the inner surface 23 of the backsheet 42 contacts the elastic members 77 and the adhesive bead 35. This configuration helps prevent any liquid that is deposited on the inner surface 23 of the backsheet 42 from migrating beyond the distal edges 66 of the side panels 62 in the rear waist region 24 and the crotch region 26. This embodiment is generally considered less desirable than other embodiments, however, because only one ply of material is present in the side panels 62. Particularly, the side panels 62 come under substantial stress when the garment is worn. Depending on the nature of the backsheet 42, single ply side panels 62 may not be strong enough for active wearers.

Figure 5A:
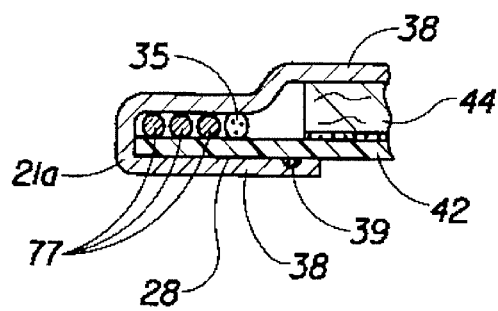
FIG. 5a is a fragmentary sectional view of an alternative embodiment of the invention.

FIG. 5a illustrates another embodiment of the present invention. In this embodiment, the topsheet 38 comprises lateral extensions 21a which wrap around the backsheet 42 and are preferably secured to the outer surface 28 of the backsheet 42 with an adhesive bead 39 or other bonding means (e.g., pressure, heat, ultrasonics, etc.). This embodiment is particularly useful when the backsheet 42 is formed from a plastic film. Since most wearer's do not like the feel of plastic next to their skin, covering the backsheet 42 with the extension 21a of the topsheet 38, which is typically made from a nonwoven fabric, presents a fabric effect on the body-facing surface 40 of the inwardly folded side panels 62 and provides the feel of cloth against the skin. (A particularly desirable material for use as the backsheet 42 is a polyfilm lined nonwoven, however, the backsheet 42 may comprise a woven or nonwoven material, polymeric films such as thermoplastic films or polyethylene or polypropylene, or composite materials such as film-coated nonwoven materials.) Another suitable construction of the side panels 62 provides the backsheet 42 comprising a laminate of a nonwoven and a polymeric film, wherein the nonwoven extends beyond the dimensions of the polymeric film to form the side panels 62.

Figure 5B:
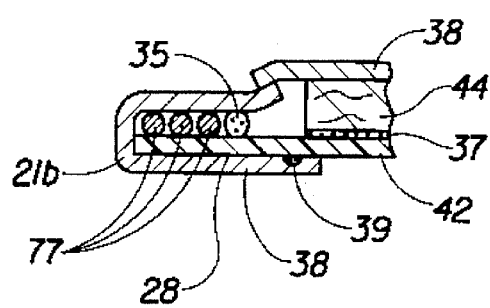
FIG. 5b is a fragmentary sectional view of another alternative embodiment of the invention.

FIG. 5b is yet another alternative embodiment of the present invention wherein the topsheet 38 has lateral extensions 21b that comprise separate members joined to the topsheet 38. The lateral extensions 21b wrap around the backsheet 42 and are preferably secured to the outer surface 28 of the backsheet 42 with an adhesive bead 39 or other bonding means (e.g., pressure, heat, ultrasonics, etc.). In a preferred embodiment, the lateral extensions 21b comprise nonwoven materials that are hydrophobic, and thus, prevent liquids deposited on the topsheet 38 from wicking beyond the liquid impervious backsheet 42 disposed in the side panels 62. The lateral extensions 21b may be joined to the topsheet 38 by any means that are well known in the art, including, but not limited to, adhesives and dynamical mechanical bonding as described in U.S. Pat. No. 4,919,783 entitled "Dynamic Mechanical Bonding Method and Apparatus" issued to Ball et al., on Apr. 24, 1990, which is herein incorporated by reference.

Figure 6:
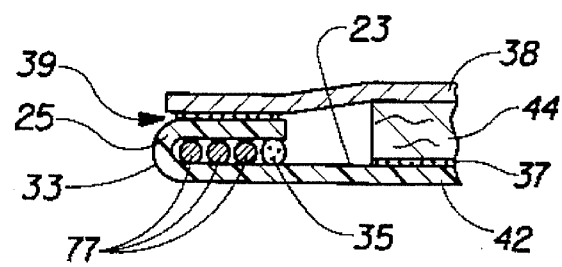
FIG. 6 is a fragmentary sectional view of another alternative embodiment of the invention.

FIG. 6 illustrates another embodiment of the present invention wherein the backsheet 42 includes a portion 25 which is wrapped around the elastic members 77 forming a longitudinal hem 33. The hem 33 is preferably formed by wrapping a portion of the backsheet 42 around the elastic members 77 and securing the backsheet 42 to itself, inboard of the elastic members 77, with a bead of adhesive 35. Preferably, the backsheet 42 is wrapped around the elastic members 77 such that the inner surface 23 of the backsheet 42 contacts the elastic members 77 and the adhesive bead 35. This configuration helps prevent any liquid that is deposited on the inner surface 23 of the backsheet 42 from migrating beyond the distal edges 66 of the side panels 62 in the rear waist region 24 and the crotch region 26. The topsheet 38 is preferably secured to the outer surface 28 of the portion 25 of the backsheet 42 that wraps around the elastic members 77 with an adhesive layer 39 or another suitable bonding means. In this configuration, the topsheet 38 will be presented against the skin of the wearer in at least the rear waist region 24.

FIG. 8 shows one alternative embodiment of the present invention having ear flaps 54 extending laterally outwardly from the distal edges 66 of the side panels 62 in the rear waist region 24. The ear flaps 54 provide a structure which, along with the front waist region 22 and the rear waist region 24, encircle the waist of the wearer. Each ear flap 54 has a proximal edge 51 and a distal edge 53. In a preferred embodiment, at least one ear flap 54 is joined to each of the side panels 62. The proximal edge 51 of the ear flap 54 is preferably joined to distal edge 66 of the side panel 62. The proximal edge 51 of the ear flap 54 may be joined to garment-facing surface 41 of the backsheet 42, or to the body-facing surface 40 of the topsheet 38, or between the topsheet 38 and the backsheet 42. The ear flaps may be joined to the side panels 62 by any means as are known in the art; for example, the ear flaps 54 may be continuously or intermittently bonded to the side panels 62 using heated or unheated adhesive, heat bonding, pressure bonding, ultrasonic bonding, dynamic mechanical bonding or any other method that is known in the art.

Figure 9:
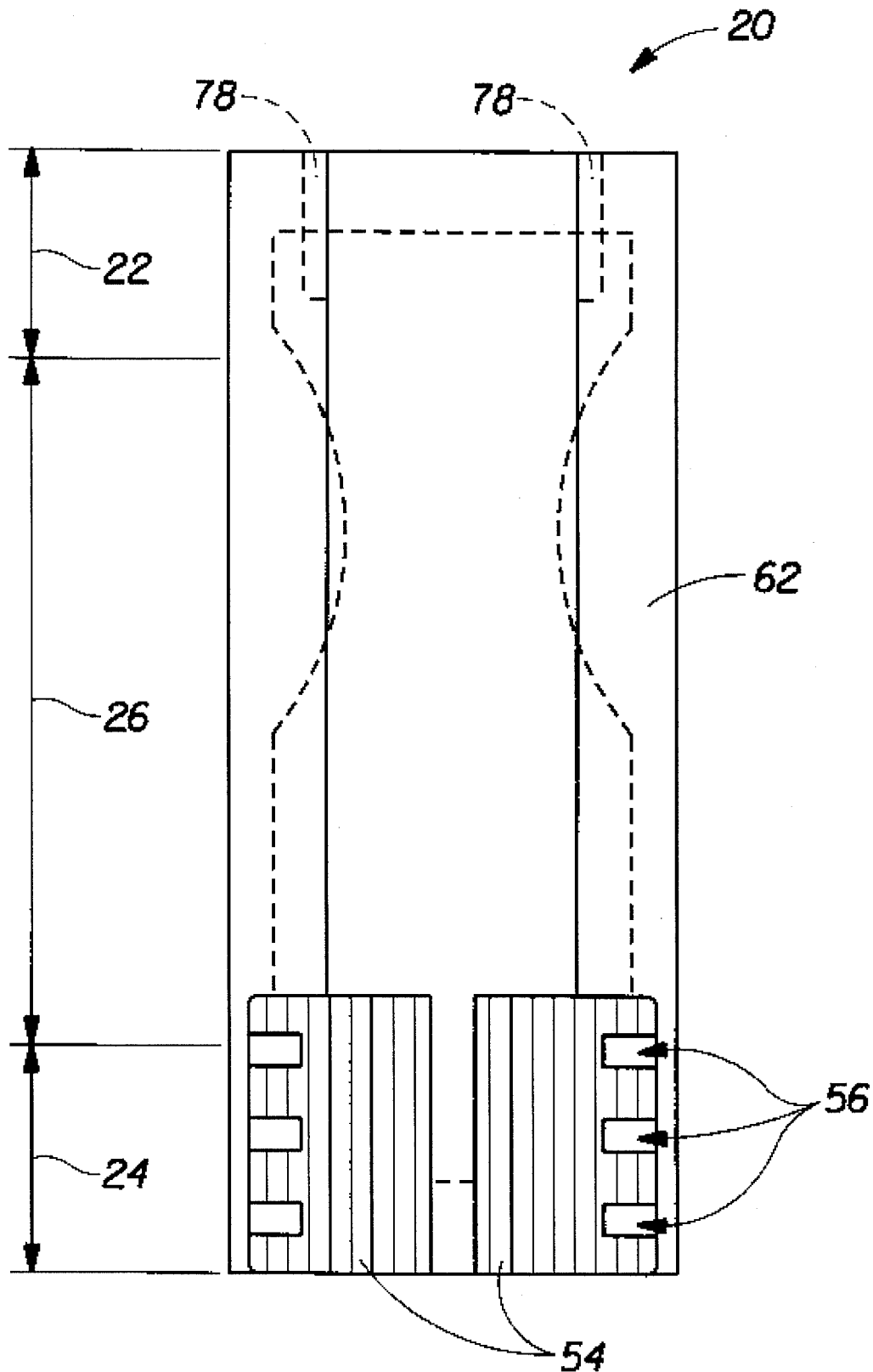
FIG. 9 is a perspective view of the garment of FIG. 1 with the side panels folded inward for packaging.

The ear flaps 54 may take on a number of different sizes, shapes, configurations and materials. In a preferred embodiment, as shown in FIG. 9, the ears flaps may be generally rectangular in shape, having dimensions of between about 2 and 8 inches in the lateral direction and between about 2 and 8 inches in the longitudinal direction; the dimensions being measured while the ear flaps 54 are in a relaxed or unextended condition. Further, the ear flaps 54 may comprise a single piece of material or two or more pieces of material operatively associated to form each ear flap 54.

The ear flaps 54 are preferably joined to the distal edges 66 of the side panels 62 in the rear waist region 24 by attachment means (not shown) such as those well known in the art. A suitable means for attaching each ear flap 54 to the side panel 62 is fusion bonding (e.g. ultrasonic, heat or pressure bonding). Alternatively, the ear flaps 54 may be intermittently or continuously bonded to the side panels 62 using adhesive, dynamic mechanical bonding or any other method that is known in the art.

The ear flaps 54 are preferably extensible in at least the lateral direction, and may be formed form any suitable extensible, stretchable, or elastomeric material. (As used herein, the term "extensible" refers to materials that can increase in at least one dimension. The term "stretchable" refers to materials that are extensible when stretching forces are applied to the material, and offer some resistance to extension. The term "elastomeric" refers to materials that extend in at least one direction when a force is applied and return to approximately their original dimensions after the force is released.) One elastomeric material that has been found to be especially suitable for use in the ear flaps 54 is a laminate of two coverstock layers with an elastomeric film sandwiched between the coverstock layers. As used herein, the term "coverstock" may include any woven or nonwoven materials. An example of a suitable coverstock material is the nonwoven material manufactured by Veratec, Inc., a Division of the International Paper Company, of Walpole, Mass., designated P-8. An example of a suitable film to be sandwiched between coverstock layers is the elastomeric film, EXX-500, manufactured by the Exxon Chemical Company of Lake Zurich, Ill. Suitable alternative materials for use as the ear flaps 54 include woven webs; nonwoven webs; films, including polymeric films; foams; laminate materials, including film laminates, nonwoven laminates, or zero strain laminates; elastomers; elastomeric scrims; composites; structural elastic-like film webs; or any combination of materials as are known in the art. U.S. Pat. No. 5,151,092 entitled "Absorbent Article with Dynamic Elastic Waist Feature Having a Predisposed Resilient Flexural Hinge" issued to Buell et al., on Sep. 29, 1992, and U.S. Pat. No. 5,167,897 entitled "Method For Incrementally Stretching a Zero Strain Stretch Laminate Web to Impart Elasticity Thereto" issued to Weber et al., on Dec. 1, 1992 describe suitable zero strain laminates and prestrained stretch laminates, and are herein incorporated by reference.

The ear flaps 54 preferably additionally comprise fastening elements 56 disposed adjacent their distal edges 53. While the fastening elements 56 may comprise any of a number of fastening elements as are known in the art such as mechanical fasteners, hook and loop type fasteners, pressure sensitive adhesives, and cohesive materials, in a preferred embodiment of the present invention, the fastening elements 56 preferably comprises tape tabs. The tape tab fasteners 56 can be any of those tape tabs well known in the art, such as the adhesive fastening tape tabs disclosed in U.S. Pat. No. 3,848,594 entitled "Tape Fastening System For Disposable Diaper" issued to Kenneth B. Buell on Nov. 19, 1974. Examples of other fastening systems, including mechanical fastening systems are disclosed in U.S. Pat. No. 4,869,724 issued to Scripps on Sep. 26, 1989; U.S. Pat. No. 4,846,815 issued to Scripps on Jul. 11, 1989; and U.S. Pat. No. 5,242,436 issued to Weil, Buell, Clear and Falcone on Sep. 7, 1993; each of which is incorporated herein by reference.

The embodiment of the present invention comprising ear flaps 54 is preferably fitted to the wearer as follows. The ear flaps 54 are initially unfolded from their folded configuration for packaging (as shown in FIG. 9) and pulled laterally outwardly in opposite directions. The rear waist region 24 is positioned under the wearer's back and the remainder of the diaper is drawn between the wearer's legs. The front waist region 22 is then positioned across the front of the wearer's waist. The ear flaps 54 are then wrapped around the wearer's waist; the side panels are tensioned and extended so as to conform to the size and shape of the wearer. The ear flaps 54 are then fastened to the front waist region 22 by means of the fastening elements 56 disposed adjacent the distal edges 53 of the ear flaps 54.

Figure 10A:
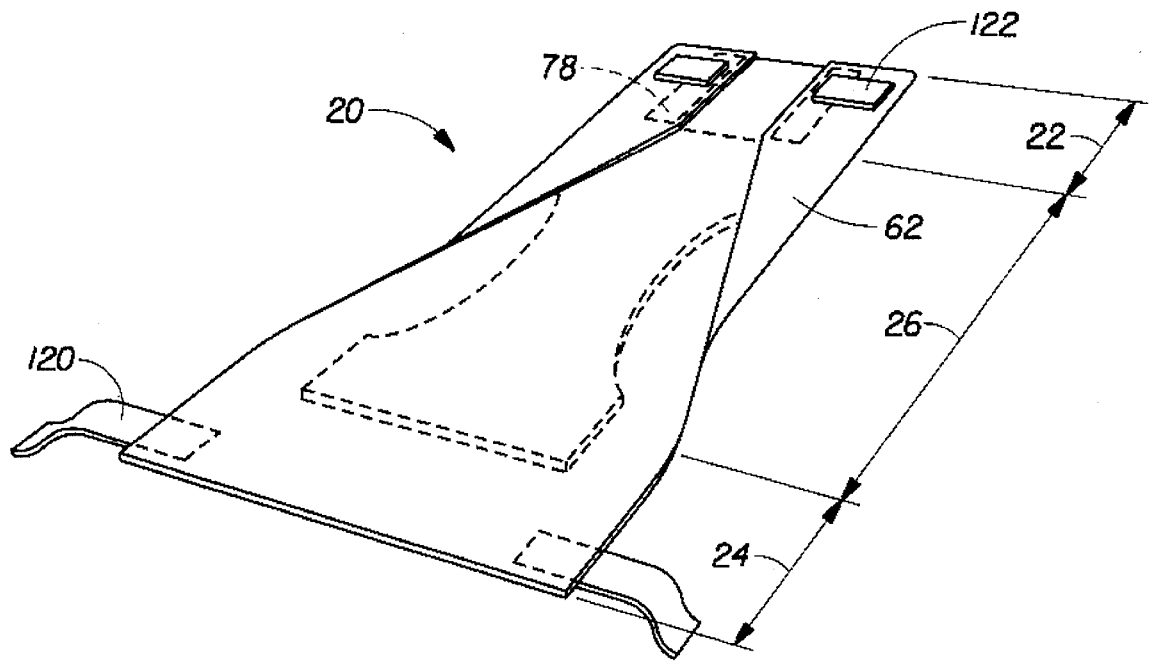
FIG. 10a is a perspective view of an alternative embodiment of the present invention having a belt.
Figure 10B:
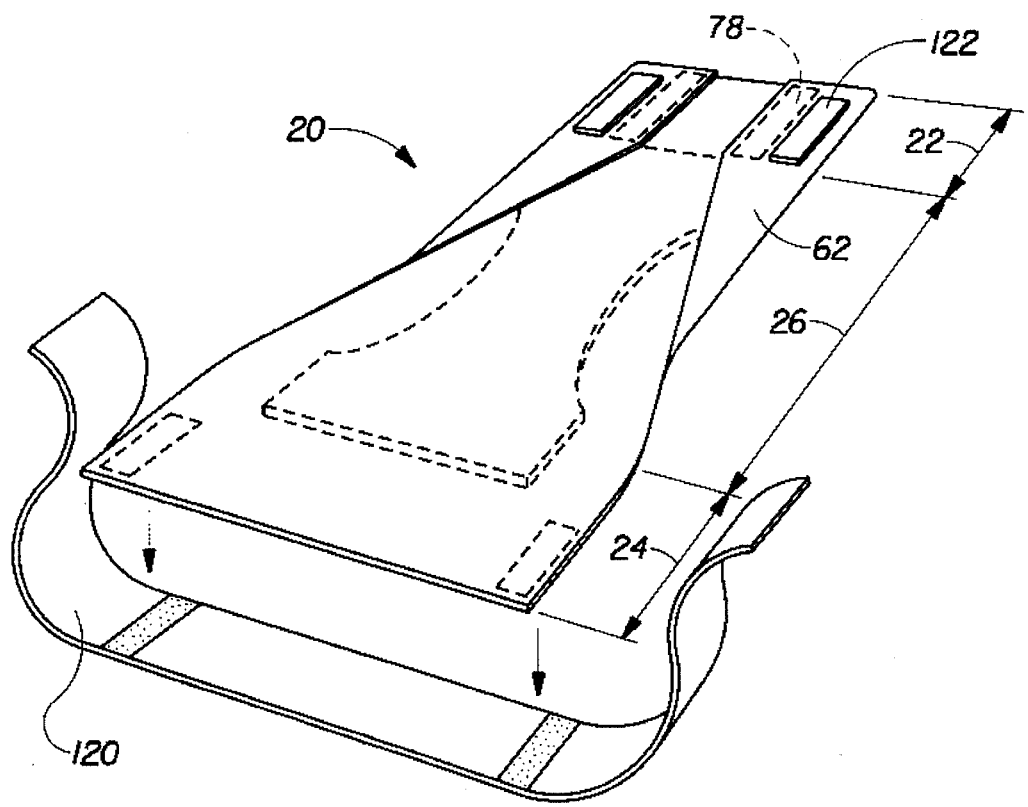
FIG. 10b is a perspective view of an alternative embodiment of the present invention having a reusable belt.

FIGS. 10a and 10b show alternative embodiments of the present invention additionally comprising belts. As shown in FIG. 10a, the belt 120 can be permanently attached to the diaper 20. Alternatively, as shown in FIG. 10b, the belt 120 can be a reusable separate element that is releasably affixed to the diaper 20 during use. In either case, the belt 120 is preferably disposed in the rear waist region 24 adjacent the end edge 32 of the diaper 20. The belt 120 may take on a number of different sizes, shapes, configurations and materials as are known in the art. An example of an absorbent article comprising belts that are suitable for use with the present invention is described in U.S. Pat. No. 4,964,860 entitled "Detachable Two Piece Absorbent Garment" issued to Gipson et at., on Oct. 23, 1990.

As shown in FIGS. 10a and 10b, the embodiments of the present invention that comprise belts preferably additionally comprise fastening elements disposed in the front waist region 22. These front waist region fastening elements 122 provide a means for fastening the front waist region 22 to the rear waist region 24 or the belt 120 when the diaper 20 is fitted to the wearer. In a preferred embodiment, at least one front waist region fastening element 122 is disposed in the front waist region 22. More preferably, as shown in FIGS. 10a and 10b, a front waist region fastening element is disposed adjacent each longitudinal edge 30 of the diaper in the front waist region 22. The front waist region fastening elements 122 may take on a number of different sizes, shapes and materials. In one preferred embodiment, the front waist region fastening elements 122 comprise pressure sensitive adhesives. Alternatively, the front waist region fastening elements 122 may comprise hook and loop type fastening material, as described in the above mentioned U.S. Pat. No. 4,964,860.

The belted diaper configuration of the present invention is preferably fitted to the wearer by first inflecting the side panel 62. This is done by either pulling laterally outwardly on the side panels 62 in the rear waist region 24, or by pulling laterally outwardly on the ends of the belt 120 which in turn provides tension to flip out the side panels 62 in the rear waist region 24. The rear waist region 24 of the diaper 20 is then placed under the wearer's back. The diaperer then pulls the remainder of the diaper 20 between the wearer's legs so that the front waist region 22 is positioned across the front of the wearer. The belt 120 is then fastened about the waist of the wearer and the front waist region fastening elements 122 are fastened to the belt 120 forming a closure between the front waist region 22 and the rear waist region 24. In this configuration, the distal edges 66 of the side panels 62 in the rear waist region 24 provide a gasket about the buttocks of the wearer and provide an inflected barrier cuff that stands up in the no motion zone of the crotch region 26.

Figure 11:
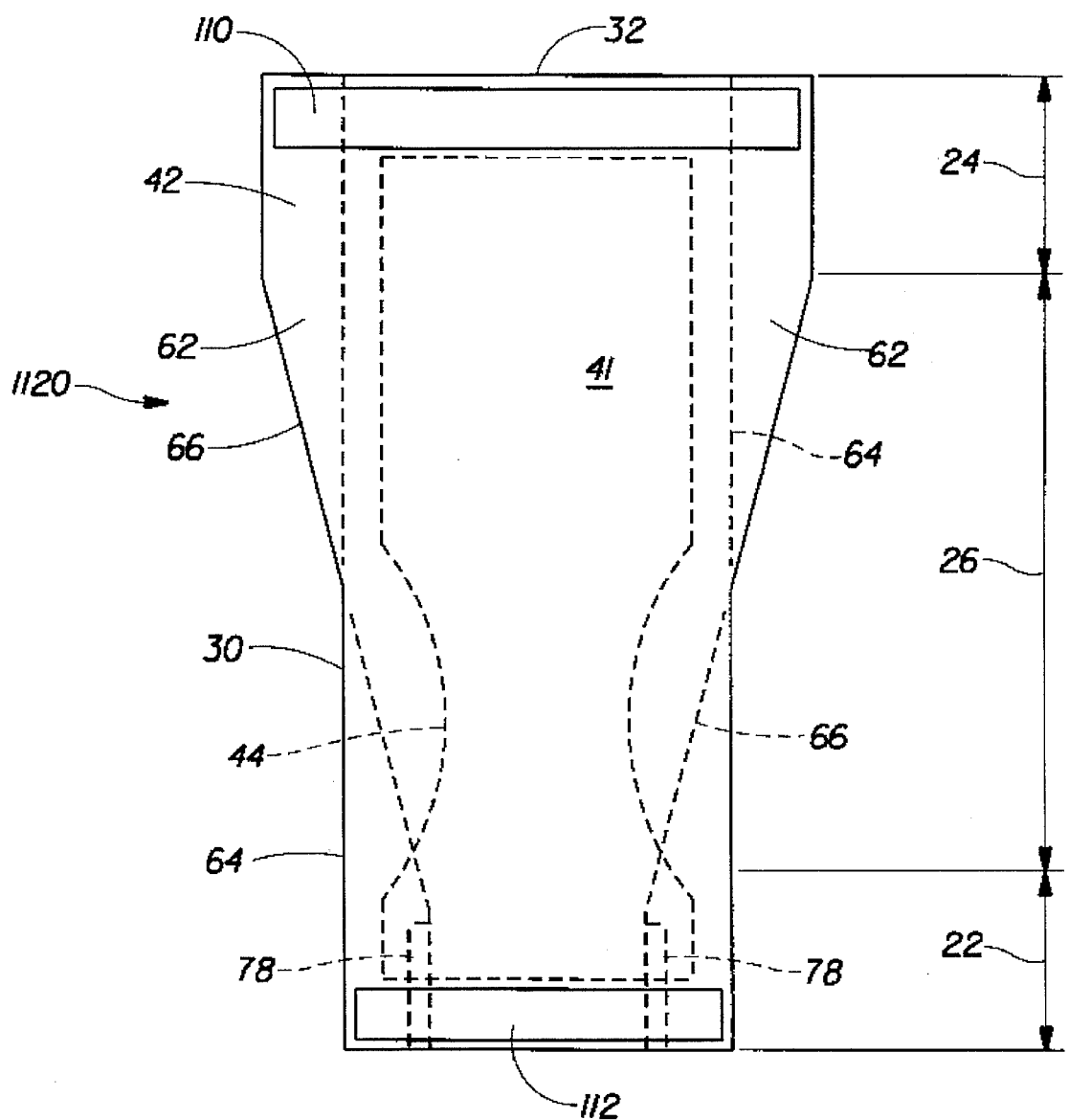
FIG. 11 is a perspective view of an alternative embodiment of the present invention having an attachment system in the front and rear waist regions, the garment-facing surface of the diaper facing the viewer.

FIG. 11 shows a pad embodiment of the present invention comprising a means for fastening the absorbent article to the wearer's pants. In a preferred embodiment, the pad 1120 comprises a front waist region securement member 112 and a rear waist region securement member 110. The front waist region securement member 112 is preferably disposed adjacent the end edge 32 of the pad 1120 in the front waist region 22, and the rear waist region securement member 110 is preferably disposed adjacent the end edge 32 of the pad 1120 in the rear waist region 24. Any adhesive, glue, mechanical fastening means, hook and loop type fastener or any other fastening means known in the art can be used for the securement members, with pressure sensitive adhesives being preferred. A suitable adhesive is Instant Lock 34-2823 manufactured by the National Starch and Chemical Company of Bridgewater, N.J. Suitable adhesive fasteners are also described in U.S. Pat. No. 4,917,697. entitled "Sanitary Napkins Having Flaps and Stress Relief Means" issued to Osborn, III et al., on Apr. 17, 1990. If a pressure sensitive adhesive is used, the adhesive is typically covered with a removable release liner in order to keep the adhesive from drying out, becoming contaminated or adhering to a surface other than the intended surface prior to use. Suitable release liners are described in the above mentioned U.S. Pat. No. 4,917,697. Any commercially available release liners commonly used for such purposes can be utilized herein. Non-limiting examples of suitable release liners are BL30MG-A SILOX E1/0 and BL30MG-A SILOX 4P/0 both of which are manufactured by the Akrosil Corporation of Menasha, Wis.

The pad embodiment of the present invention, as shown in FIG. 11, is fitted to the wearer by first inflecting the side panels 62. This is done by pulling laterally outwardly on the side panels 62 in the rear waist region 24. The diaperer then removes any release liner(s) and positions the pad into the wearer's undergarment. Preferably, the front waist region 22 should be positioned in the front of the wearer's undergarment and the rear waist region 24 should be placed in the rear of the wearer's undergarment. In this configuration, the distal edges 66 of the side panels 62 in the rear waist region 24 provide gasketing about the wearer's buttocks while the distal edges 66 of the side panels 62 in the crotch region 26 stand up to provide an inflected barrier cuff in the wearer's no motion zone.

Figure 12A:
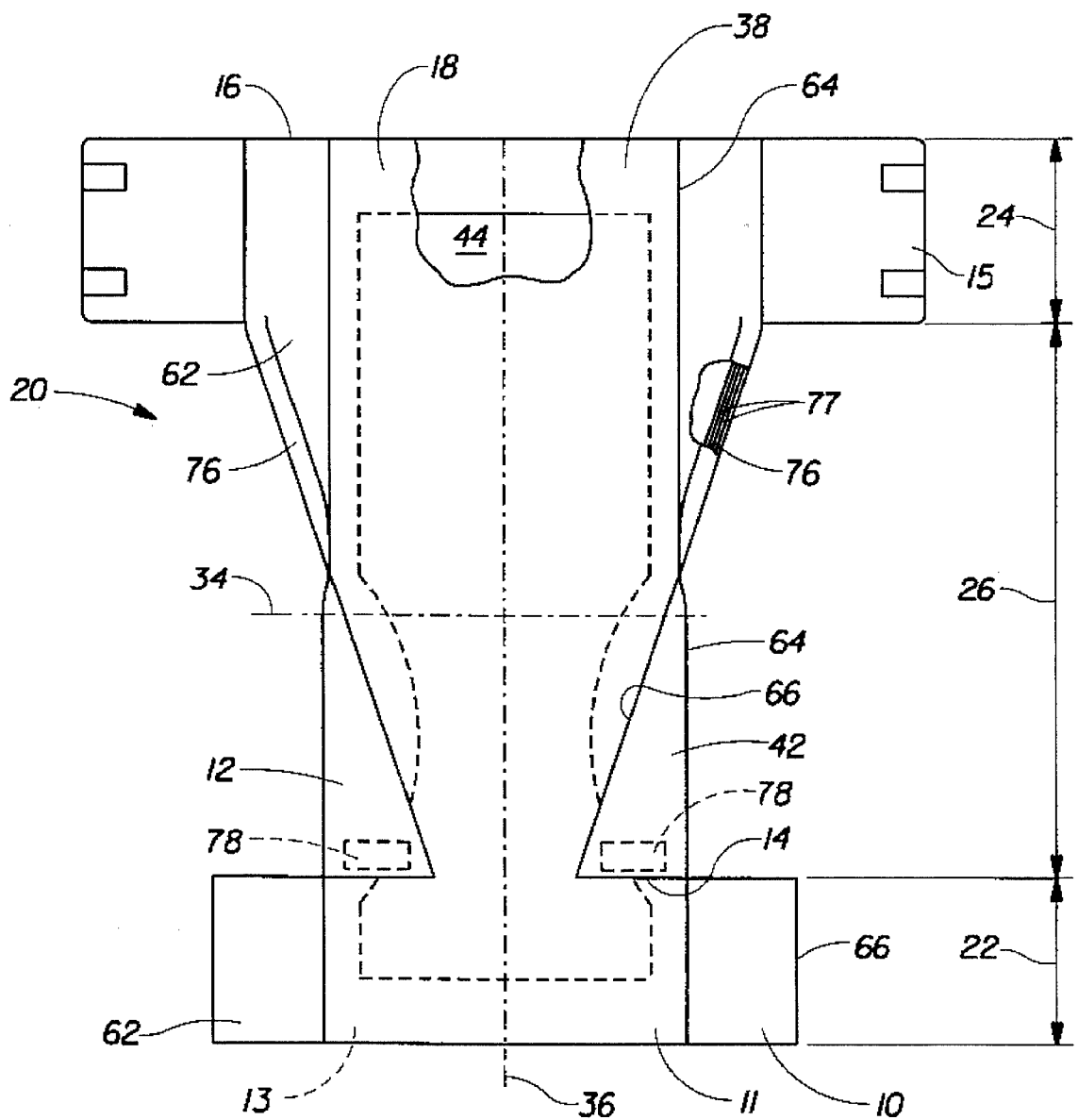
FIG. 12a is a perspective view of an alternative embodiment of the present invention wherein the side panels are separated between the front waist region and the crotch region, the body-facing side of the diaper faces the viewer.
Figure 12B:
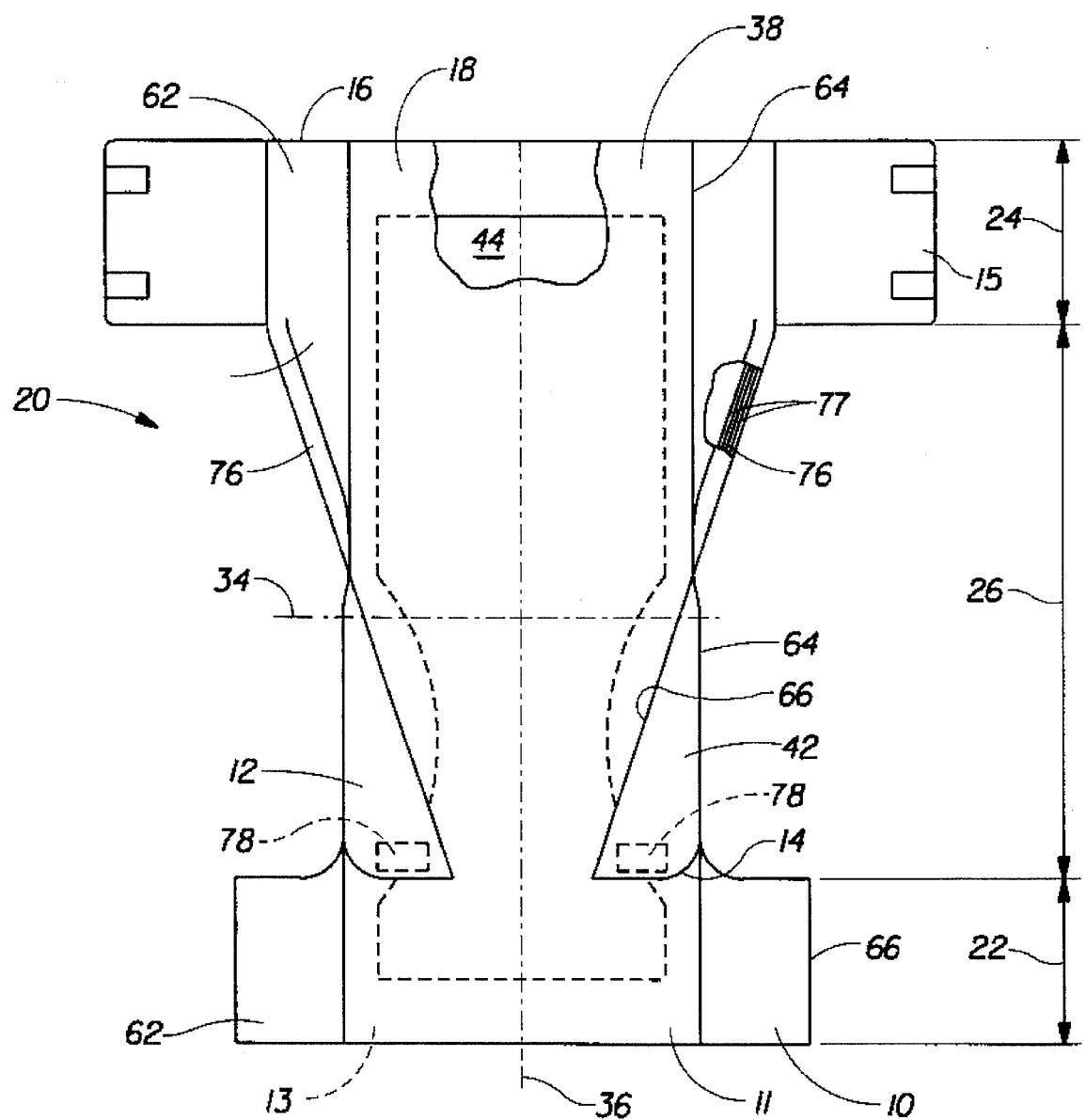
FIG. 12b is a perspective view of an altenative embodiment of the diaper shown in FIG. 12a wherein the separation in the side panels between the front waist region and the rear waist region is curvilinear, the body-facing side of the diaper faces the viewer.

FIGS. 12a and 12b show yet other alternative embodiments of the present invention. The diapers 20 shown in FIGS. 12a and 12b each have a front waist region 22, a rear waist region 24, a crotch region 26, a lateral centerline 34 and a longitudinal centerline 36. The diaper 20 preferably further comprises a liquid pervious topsheet 38, a liquid impervious backsheet 42, an absorbent core 44, side panels 62, a spacing means 76 (such as the elastic members 77), and closing means 78. (The spacing means 76 and the closing means 78 may comprise any of those hereinbefore described with regard to this invention.) In the embodiments shown in FIGS. 12a and 12b, the side panels 62 each include a front ear flap section 10 located in the front waist region 22, and a barrier cuff section 12 that extends longitudinally from the crotch region 26 to at least the rear waist region 24. Each side panel 62 has a proximal edge 64 and a distal edge 66. Each barrier cuff section 12 has a first end edge 14 located longitudinally inboard of the front ear flap section 10 and a second end edge 16 located in or juxtaposed the rear waist region 24. (As used herein, the term "longitudinally inboard" is defined as the direction toward the lateral centerline 34 of the diaper 20.)

In one preferred configuration of the embodiments shown in FIGS. 12a and 12b, the distal edges 66 of the side panels 62 are unsecured to any underlying structure of the diaper 20 in the front waist region 22 and the rear waist region 24 while the distal edge 66 of at least a portion of the barrier cuff section 12 juxtaposed the first end edge is secured laterally inboard of the proximal edge 64 by the closing means 78. This configuration inverts the second end edges 16 of the side panels 62 with regard to the first end edges 14, thus creating an inflected barrier cuff that stands up in the crotch region 26 when the diaper 20 is fitted to a wearer. This configuration also provides a front ear flap 10 in the front waist region 22 of the diaper 20 that can be extended laterally outwardly to provide a greater amount of material in the front waist region 22 to better contain exudates or to provide a greater area to which the rear waist region 24 may be joined when the diaper 20 is fitted to a wearer. This embodiment of the present invention can also be provided with rear waist region ear flaps 15. The rear waist region ear flaps 15 may comprise any of the materials and may be joined in any way as previously discussed in this application with regard to the ear flaps 54. Further, the rear waist region ear flaps 15 may be permanently joined with said front waist region 22 to form a pant.

Figure 13:
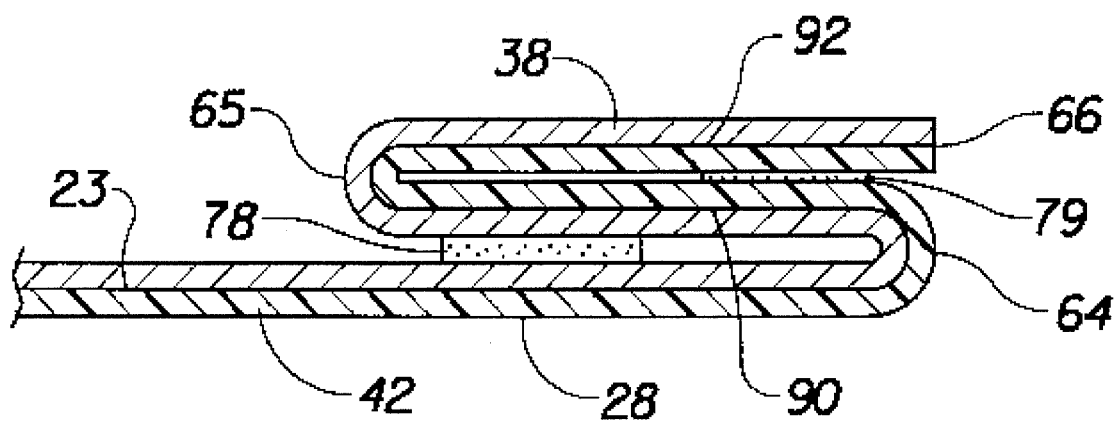
FIG. 13 is a fragmentary sectional view of the absorbent article showing a z-fold.
Figure 14:
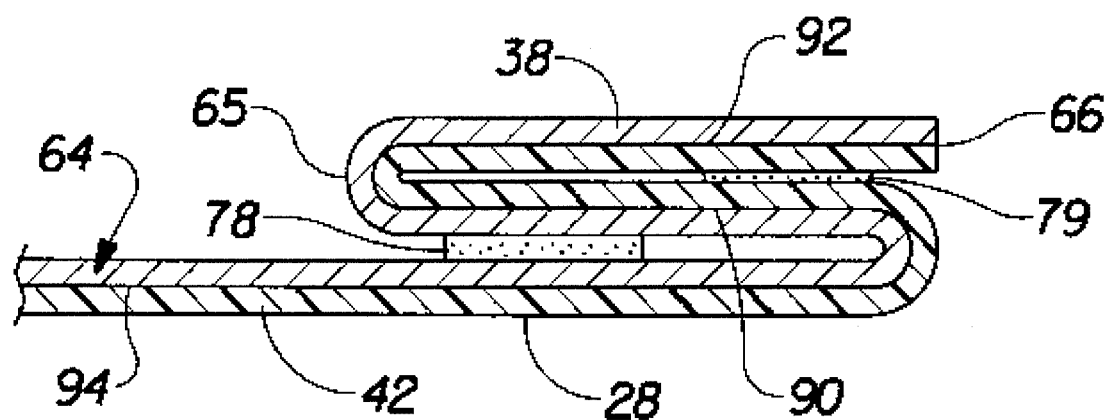
FIG. 14 is a fragmentary sectional view of the absorbent article showing a z-fold.

In an alternative configuration of the embodiments shown in FIGS. 12a and 12b, the inflected barrier cuffs may comprise side panels 62 that are "z-folded" two examples of which are shown in FIGS. 13 and 14. As used herein, the term "z-folded" refers to side panels 62 that comprise at least some portion which is folded over itself such that at least one surface of the side panel is juxtaposed and in an overlapping configuration with another portion of the same surface of the side panel. The z-folded configuration provides the benefits described above with regard to an inflected barrier cuff while ensuring that a skin-friendly material is against the skin of the wearer throughout the length of the barrier cuff. Some preferred embodiments of z-folded side panels are disclosed in co-pending U.S. patent application Ser. No. 08/310,173 filed on Sep. 21, 1994 in the names of Benjamin et at., which is hereby incorporated by reference herein.

As shown in FIG. 13, the first segment 90 is preferably folded inwardly (toward the longitudinal centerline) over the topsheet 38 in at least the crotch region 26. The second segment 92 is preferably folded outwardly (away from the longitudinal centerline) over the first segment 90. This creates a fold 65 intermediate the proximal edge 64 and the distal edge 66 of the side panel 62 in at least the crotch region 26. Further, this "z-fold" configuration provides a skin-friendly surface against the wearer throughout the length of each side panel 62.

In preferred embodiments, at least a portion of the first segment 90 is secured to the underlying structure (topsheet 38) intermediate the proximal edge 64 and the fold 65 by the first closing means 78 and at least a portion of the second segment 92 intermediate the fold 65 and the distal edge 66 is secured to the underlying structure (backsheet 42 of first segment 90) by the second closing means 79. Therefore, the fold 65 is closed in the crotch region 26 (i.e., it is not open nor capable of being spaced away from the body-facing surface 40) and the topsheet 38 of the side panel 62 is provided in a position such that it will be in contact with a wearer's skin when the diaper 20 is donned. In an alternative embodiment, as shown in FIG. 14, each side panel 62 additionally comprises a third segment 94 which comprises the proximal edge 64. In such configurations, the first closing means 78 secures at least a portion of the first segment 90 over the third segment 94 and the second closing means 79 secures at least a portion of the second segment 92 over the first segment 90.

The diapers shown in FIGS. 12a and 12b may be manufactured using the following method. First, a generally rectangular chassis 18 is provided having a inner surface 11, an opposing outer surface 13, a front waist region 22, a rear waist region 24, a crotch region 26 located between the front waist region 22 and the rear waist region 24, a lateral centerline 34, a longitudinal centerline 36, and a pair of laterally opposed side panels 62 extending longitudinally from the front waist region 22 to the rear waist region 24. The side panels each have a proximal edge 64, a distal edge 66 and a second end edge 16 located in the rear waist region 24.

The side panels 62 are separated between the front waist region 22 and the crotch region 26 forming a first end edge 14 located in the crotch region 26. The side panels 62 may be separated by any means as are known in the art, including, but not limited to, slitting, cutting, tearing, or perforating, using knives, lasers, heat, pressure, ultrasound or any combination of these. In one preferred embodiment, as shown in FIG. 12a, the separation is a relatively straight separation in a direction relatively parallel to the lateral centerline 34. However, in other preferred embodiments, one of which is shown in FIG. 12b, the separation is curvilinear or at an angle to lateral centerline. (As used herein, the term "curvilinear" refers to any separation that is not relatively straight, but rather comprises at least one curve.)

Either before or after the separation step has been completed, the side panels 62 are folded over the chassis 18. Once the separation step has been performed, a portion of the side panel juxtaposed the first end edge 14 is secured to the inner surface 11 of the chassis 18 in the crotch region 26. This ensures that at least a portion of the side panel 62 juxtaposed the first end edge 14 is inverted relative to the second end edge 16, thus, providing an inflected barrier cuff that stands up in the crotch region when the diaper is fitted to a wearer. (If a z-fold configuration is desired, at least a portion of each side panel 62 juxtaposed the first end edge 14 is folded back upon itself and preferably secured thereto.) If a pant configuration is preferred, the rear waist region ear flaps 15 are permanently joined with said front waist region 22 to form the pant. A more detailed discussion of methods for manufacturing diapers with inflected barrier cuffs is disclosed in co-pending U.S. patent application Ser. No. 08/260,638 which was filed on Jun. 16, 1994 in the names of Sageser et al., which is hereby incorporated by reference herein.

The configuration of the diaper 20 shown in FIGS. 12a and 12b is preferably fitted to the wearer by extending the side panels 62 laterally outwardly in at least the rear waist region 24. If desired, the side panels 62 may be extended laterally outwardly in the front waist region 22 forming front ear flaps 10. (If the diaper 20 was manufactured with perforations at the separation between the front waist region 22 and the crotch region 26, the user will have to tear or otherwise completely separate the perforations to release the front ear flaps 10 from the barrier cuff section of the side panels 62.) The rear waist region 24 is placed under the wearer's back and the remainder of the diaper is drawn between the legs of the wearer. The front waist region 22 is then positioned across the front waist of the wearer. The rear waist region 24 is then wrapped around the wearer's waist and joined to the front waist region 22. The front ear flaps 10, when extended provide a surface to which the rear waist region 24 may be joined. In embodiments comprising rear waist region ear flaps 15, the rear waist region ear flaps 15 may be joined to the front waist region 22 or the front ear flaps 10.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a front waist region, a rear waist region, a crotch region between said front waist region and said rear waist region, a pair of longitudinal edges, a lateral centerline and a longitudinal centerline, the absorbent article comprising:

a chassis comprising a liquid pervious topsheet; a liquid impervious backsheet joined with said topsheet; an absorbent core interposed between said topsheet and said backsheet, said absorbent core having a pair of opposed side edges, a pair of longitudinally extending side panels, each of said side panels including a front ear flap section located in said front waist region; a barrier cuff section having a first end edge located longitudinally inboard of said front ear flap section; a second end edge located in said rear waist region; a proximal edge disposed adjacent one of said side edges of said absorbent core and a distal edge spaced apart from said proximal edge;

spacing means joined along said distal edge of each said barrier cuff section; and closing means for securing at least a portion of said barrier cuff section juxtaposed said first end edge to the absorbent article inboard of said proximal edge;

said distal edges being unsecured to any underlying structure of the absorbent article in said front waist region and said rear waist region such that said distal edges form said longitudinal edges in said front waist region and said rear waist region; and said distal edge of said barrier cuff section being secured laterally inboard of said proximal edge in said crotch region such that said second end edges of said side panels located in said rear waist region are inverted relative to said first end edges to form an inflected barrier cuff that stands up in said crotch region when the absorbent article is fitted to a wearer.

2. The absorbent article of claim 1 additionally comprising an ear flap joined to and extending outwardly from each said side panel in the rear waist region.

3. The absorbent article of claim 2 wherein said ear flaps additionally comprise a fastening means for securing the absorbent article about the waist of the wearer.

4. The absorbent article of claim 3 wherein said fastening means comprises a tape tab having one end secured to said ear flap and a second end for attachment to said front waist region.

5. The absorbent article of claim 2 wherein said ear flaps comprise a stretch laminate comprising a layer of elastomeric film sandwiched between two layers of nonwoven fabric.

6. The absorbent article of claim 1 wherein said side panels are z-folded in at least said barrier cuff section.

7. A disposable absorbent article having a front waist region, a rear waist region, a crotch region between said front waist region and said rear waist region, a pair of longitudinal edges, a lateral centerline and a longitudinal centerline, the absorbent article comprising:

a chassis comprising a liquid pervious topsheet; a liquid impervious backsheet joined with said topsheet; an absorbent core interposed between said topsheet and said backsheet, said absorbent core having a pair of opposed side edges, a pair of longitudinally extending side panels, each of said side panels including a front ear flap section located in said front waist region; a barrier cuff section having a first end edge located longitudinally inboard of said front ear flap section; a second end edge located in said rear waist region; a proximal edge disposed adjacent one of said side edges of said absorbent core and a distal edge spaced apart from said proximal edge;

spacing means joined along said distal edge of each said barrier cuff section; and closing means for securing at least a portion of said barrier cuff section juxtaposed said first end edge to the absorbent article inboard of said proximal edge;

said front ear flap sections being separably joined to said barrier cuff sections, wherein said distal edges of said ear flap sections may be separated from said barrier cuff section when the absorbent article is fitted to a wearer such that said distal edges of said front ear flap sections form said longitudinal edges in said front waist region;

said distal edges being unsecured to any underlying structure of the absorbent article in said rear waist region such that said distal edges form said longitudinal edges in said rear waist region; and said distal edge of said barrier cuff section being secured laterally inboard of said proximal edge in said crotch region such that said second end edges of said side panels located in said rear waist region are inverted relative to said first end edges to form an inflected barrier cuff that stands up in said crotch region when the absorbent article is fitted to said wearer.

8. The absorbent article of claim 7 additionally comprising an ear flap joined to and extending outwardly from each said side panel in the rear waist region.

9. The absorbent article of claim 8 wherein said ear flaps additionally comprise a fastening means for securing the absorbent article about the waist of the wearer.

10. The absorbent article of claim 7 wherein said ear flap is permanently joined in said front waist region to form a pant.

11. The absorbent article of claim 8 wherein said ear flaps comprise a stretch laminate comprising a layer of elastomeric film sandwiched between two layers of nonwoven fabric.

12. The absorbent article of claim 7 wherein said side panels are z-folded in at least said barrier cuff section.

* * * * *